US005948401A

United States Patent [19]

Donabedian et al.

[11] Patent Number: 5,948,401

[45] Date of Patent: Sep. 7, 1999

[54] CATIONIC THERAPEUTIC SYSTEMS

[75] Inventors: David Hagop Donabedian, Somerset, N.J.; Donna Jean Eng, Hartsdale, N.Y.; Lawrence Marlin, Bridgewater, N.J.

[73] Assignee: Union Carbide Chemicals & Plastics Technology Corporation, Danbury, Conn.

[21] Appl. No.: 08/772,651

[22] Filed: Dec. 23, 1996

Related U.S. Application Data

[60] Provisional application No. 60/009,101, Dec. 22, 1995.

[51] Int. Cl.[6] .......................... A61K 47/32; A61K 47/34; A61K 47/36

[52] U.S. Cl. .......................... 424/78.04

[58] Field of Search .......................... 424/78.04

[56] References Cited

U.S. PATENT DOCUMENTS

| | | | |
|---|---|---|---|
| 4,012,444 | 3/1977 | Lunts et al. | 260/559 S |
| 4,168,112 | 9/1979 | Ellis et al. | 351/160 |
| 4,252,984 | 2/1981 | Manoury et al. | 564/349 |
| 4,321,261 | 3/1982 | Ellis et al. | 424/180 |
| 4,436,730 | 3/1984 | Ellis et al. | 424/180 |
| 4,605,691 | 8/1986 | Balazs et al. | 524/27 |
| 4,767,463 | 8/1988 | Brode et al. | 106/162 |
| 4,913,743 | 4/1990 | Brode et al. | 106/162 |
| 4,938,951 | 7/1990 | Leung et al. | 424/59 |
| 5,093,126 | 3/1992 | Jani et al. | 424/428 |
| 5,246,698 | 9/1993 | Eschiner et al. | 424/78.04 |
| 5,358,706 | 10/1994 | Marlin et al. | 424/78.04 |
| 5,401,327 | 3/1995 | Ellis et al. | 134/42 |
| 5,407,919 | 4/1995 | Brode et al. | 514/57 |

FOREIGN PATENT DOCUMENTS

| | | | |
|---|---|---|---|
| WO9500618 | 1/1995 | WIPO | 424/78.04 |

*Primary Examiner*—Peter F. Kulkosky
*Attorney, Agent, or Firm*—W.K. Volles

[57] ABSTRACT

The present invention relates to delivery systems comprising a cationic polymer, optionally in conjunction with an anionic polymer, to deliver cationic therapeutic agents and their application to a mucosal surface. In particular, these delivery systems are well suited for the treatment of intraocular pressure and glaucoma by way of a sustained delivery system.

21 Claims, 3 Drawing Sheets

5000
ENERGY WIDTH AREA %
400.78 3.72 6551 100.0

COUNTS 416.2 411.2 406.2 401.2 396.2 391.2
BINDING ENERGY (eV)

10000
ENERGY WIDTH AREA %
402.06 1.57 6870 54.0
399.29 3.16 5854 46.0

COUNTS 416.4 411.4 406.4 401.4 396.4 391.4
BINDING ENERGY (eV)

CATIONIC THERAPEUTIC SYSTEMS

This application claims benefit of Provisional Application No. 60/009,101, filed Dec. 22, 1995.

FIELD OF THE INVENTION

The present invention relates to the use of cationic polymers to deliver cationic therapeutic agents to a mucosal surface, e.g., the eye. The invention also relates to the use of cationic polymers in conjunction with anionic polymers to deliver the cationic therapeutic agents to the mucosal surface.

BACKGROUND OF THE INVENTION

The delivery of therapeutic agents to mucosal surfaces has inherent difficulties due to the moist nature of the mucosal surfaces. This problem is particularly acute in the delivery of therapeutic agents to the surface of the eye where the washing effects of the tear film often removes much of the therapeutic agent. For glaucoma medications, for example, the result is a small pulse of drug is delivered to the target ocular tissues, while the majority of the drug is absorbed systemically.

The delivery of anionic therapeutic agents utilizing cationic polymers such as for example, cationic polysaccharides to bind the anionic therapeutic agent to the mucosal surface has been described, for example, in U.S. Pat. No. 5,358,706 issued Oct. 25, 1994. When the therapeutic agent is anionic, e.g., hyaluronic acid, the adhesion to the cationic substrate polymer is generally acceptable and the delivery of the anionic therapeutic agent to the mucosal surface can be controlled. However, in the case of cationic therapeutic agents, e.g., beta-blockers, the naturally occurring attractive forces between the positive and negatively charged species in the cationic/anionic systems is absent. Thus, both the adhesion to the cationic polymer substrate and the control of the delivery of the cationic therapeutic agent to mucosal surface can be uncertain.

Accordingly, there is a need for a method for treating mucosal surfaces such as, for example, the eye, in order to retain an active agent for a longer period of time. Moreover, there is a continuing need to produce ophthalmic formulations that are characterized as long lasting (sustained release) and are comfortable to the eye.

SUMMARY OF THE INVENTION

This invention pertains to topical, substantive delivery systems for mucosal tissues comprising an aqueous composition of a cationic polysaccharide and a cationic therapeutic agent. A preferred delivery system in accordance with the present invention comprises a cationic polysaccharide and an anionic polymer to function as a bridging agent between the cationic polysaccharide and the cationic therapeutic agent. The cationic therapeutic agents which can be delivered by the delivery systems of the present invention include, for example, agents known in the art as "basic actives", e.g., timolol and betaxolol and drugs such as pilocarpine, epinephrine, and carbachol. This invention is particularly useful for the treatment of lowering and controlling intraocular pressure ("IOP") in the treatment of glaucoma as well as providing for decreased discomfort as usually associated with the use of such drugs.

DETAILED DESCRIPTION OF THE INVENTION

Figure 1:
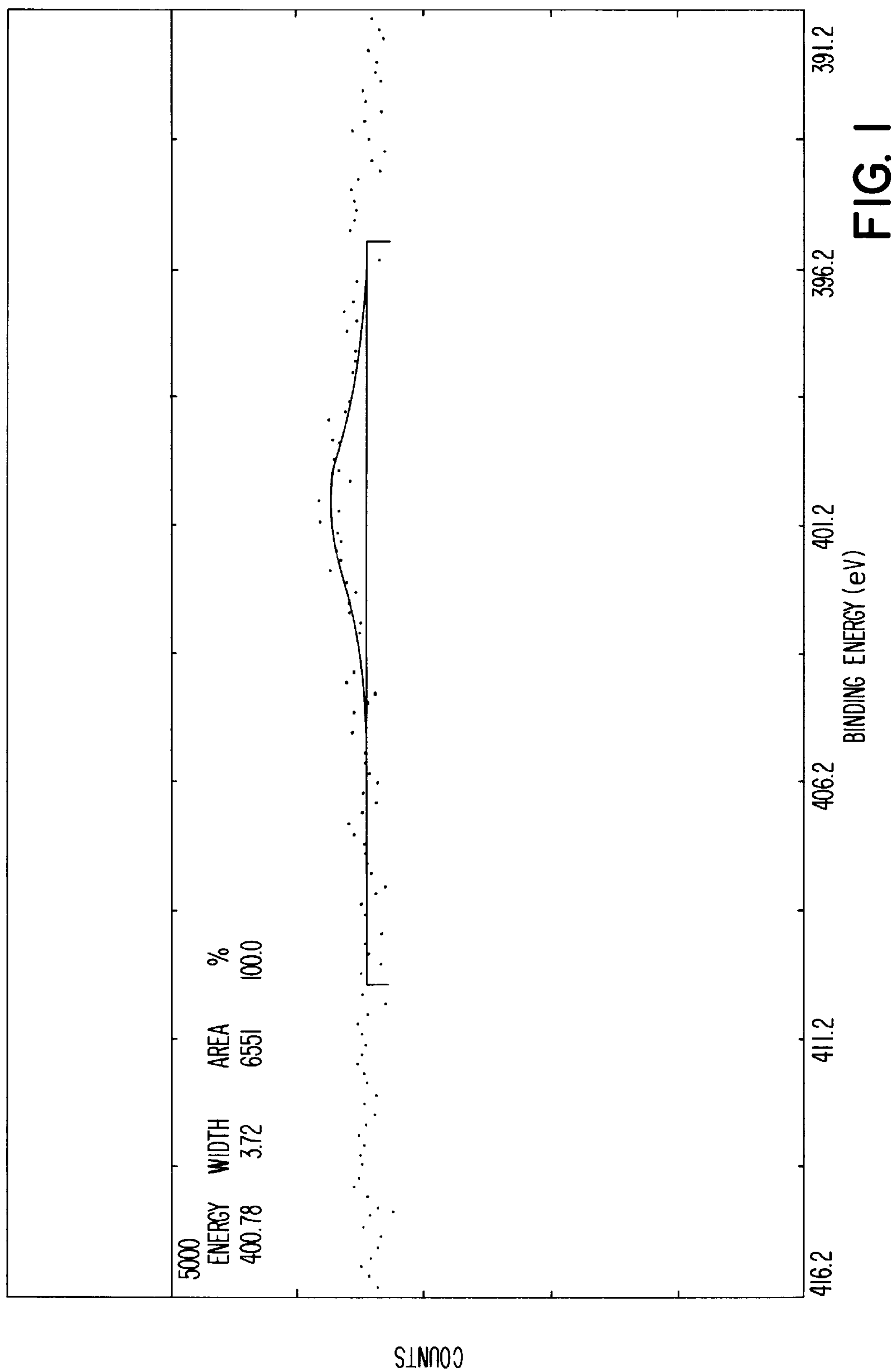
FIG. 1 is an ESCA spectrum of a high resolution scan from pilocarpine HCl.

Mucosal surfaces in the body include, but are not limited to, the outer covering or globe of the eye, the inside lining of the mouth, nose and vagina. These surfaces are generally soft, moist tissue. For example, the globe or outer covering of the eye is comprised of non-keratinized epithelium (Bloom, W. and Fawcett, D. W., *A TEXTBOOK OF HISTOLOGY,* 10th Ed., W. B. Saunders Co., Philadelphia 1975). The surface of the eye is continuously coated with water from the tear ducts which frequently washes material away from the outer coating of the eye. Unlike the skin which is comprised of keratin, the mucosal surfaces of the body are not comprised of keratin.

The cationic polysaccharide polymers which are useful in the present invention are those which are substantive to mucosal surfaces and include, but are not limited to: the starch and cellulose families; pectin; chitin; chitosan; guar; and the like. Substantivity of the cationic therapeutic agent and cationic polysaccharide polymer combination is characterized by an increase of the cationic polysaccharide polymer on the mucosal surface. Substantivity can be measured, for example, through the use of an ocular fluorimeter. The cationic polysaccharide polymer is fluorescently tagged by reaction with fluorescein as described in the procedure of De Balder and Granath for labeling dextrans; *Carbohydrate Research,* 30 (1973) 375–378.

Preferably, the cationic polysaccharides are substituted with greater than about 0.1, preferably from about 0.15 to 1.0 and more preferably from about 0.2 to 1.0, mole per mole of polysaccharide of a quaternary nitrogen compound having hydrocarbon substituents with from 1 to about 4 carbon atoms per substituent. As used herein, the term "substituent" is made with reference to substituents other than the substituent which is connected to the polysaccharides, although it is typical for the connecting substituent to also have up to about 4 carbon atoms. Preferably, the connecting substituent comprises an alkoxyalkyl radical with a least 2 carbon atoms separating the oxygen atom from the nitrogen atom. Preferably, the other substituents will be either methyl or ethyl and the total number of carbon atoms in such other substituents will be from about 3 to 6, more preferably about 4. A preferred regent suitable for substitution onto the polysaccharide is 2,3 epoxypropyl trimethyl ammonium chloride. Preferably, the type of quaternary substitutent and substitution level is effective to provide substantivity to the mucosal surface and a clear solution, even when the solution contains isotonic salt, e.g., 9 grams of sodium chloride per liter of water. Further details concerning the preparation of suitable cationic polysaccharides is known to those skilled in the art.

The molecular weight of the cationic polysaccharides suitable for use in accordance with the present invention typically ranges from about 10,000 to 1,000,000 grams per gram mole ("g/mol") and preferably ranges from about 20,000 to 800,000 g/mol. As used herein, the term "molecular weight" means weight average molecular weight. Methods for determining weight average molecular weight of polysaccharides are known to those skilled in the art. One preferred method for determining molecular weight is low angle laser light scattering. The viscosity of the cationic polysaccharides typically ranges from about 5 to 10,000 centipoise, preferably from about 10 to 2,000 centipoise. Unless otherwise indicated, as used herein the term "viscosity" refers to the viscosity of a 2.0 weight percent aqueous solution of the polymer measured at 25° C. with a Brookfield viscometer. Such viscosity measuring techniques are known in the art.

Preferred cationic polysaccharides are water soluble, cationic cellulosics which include, but are not limited to, water soluble quaternary nitrogen-containing cellulose ethers characterized by varying degrees of cationic substitution and molecular weight. These materials are available from Union Carbide Corporation, Danbury, Conn. As used herein, the term "water soluble" is made with reference to a 1 weight percent aqueous solution.

The cationic therapeutic agents suitable for use in accordance with the present invention are those therapeutic agents that bear, or are capable of bearing, a positive charge during formulation or use of the final product. Such base actives are known in the art, see e.g., U.S. Pat. Nos. 5,093,126, 4,252,984, and 4,012,444. These materials often have the desired effects of controlling and lowering IOP.

Examples of these cationic therapeutic agents are: beta blockers, including but not limited to, betaxolol, timolol, labetalol, propranolol, bupranolol, befunolol, acebutolol, salbutamol, atenulol, isoxaprolol, esmalol, pindolol, hepunolol, carpranolol, metaprolol, azotinolol, carteolol, diacetolol, and the like; and the following classes of drugs which are used in the treatment of ocular hypertension and glaucoma: epinephrine, pilocarpine, proepinephrine, norepinephrine, pronorepinephrine, clonidine and clonidine derivatives and carbachol. Further, the cationic polymers may have ameliorating properties, thus providing for decreased discomfort usually associated with the use of such therapeutic agents. Such cationic therapeutic agents are commercially available.

In a broad sense, the relative proportion of cationic polymer to cationic therapeutic agent is not narrowly critical. The relative weight ratio of cationic polymer to cationic therapeutic agent will preferably range from 1:1 to about 200:1, more preferably from about 2:1 to about 100:1 and most preferably from about 10:1 to about 50:1.

Typically, the amount of cationic therapeutic agent is at least about 0.0001 weight percent, preferably from about 0.0005 weight percent to about 5.0 weight percent, more preferably from about 0.001 weight percent to about 2.0 weight percent and most preferably from about 0.01 weight percent to less than about 1.0 weight percent based on the total weight of the composition, i.e., cationic therapeutic agent, cationic polysaccharide, water and other ingredients.

The amount of cationic polysaccharide polymer provided may also vary widely. In a preferred embodiment, the cationic polymer is provided in an amount sufficient to be substantive to the mucosal surface, i.e., has an affinity for such body surface. Typically, the amount of cationic polymer is at least about 0.0005 weight percent, preferably from about 0.0025 weight percent to about 20.0 weight percent and more preferably from about 0.005 weight percent to about 10 weight percent of the total weight of the composition.

Through selection and optimization of the various related structural parameters influencing viscosification, cationic polysaccharide polymers of this invention can be produced which provide a desired level of viscosity, within a potentially wide range of values. Aqueous solutions containing 0.5 weight percent concentrations cationic polysaccharide polymers of this invention will usually have a Brookfield viscosity at 25° C. of less than 50 centipoise (cps), and preferably from about 5 to about 30 cps.

One aspect of the present invention provides methods for delivery of cationic therapeutic agents to mucosal surfaces with a cationic polysaccharide and delivery systems comprising the cationic therapeutic agents and the cationic polysaccharide. Preferably, the cationic therapeutic agent has an affinity for one or both of the body surface or the cationic polysaccharide. Without being bound to any particular theory, it is believed that the cationic therapeutic agent, due to its mobility and size, can easily gain access to the mucosal surface. Once being bound to that surface, either electrostatically or covalently, the cationic polysaccharide can then deposit over the drug in a loop type of conformation and hence entrap it on the surface, thus holding it on the surface longer and increasing drug residence time into the surface. Thus, enhanced effects of sustained drug delivery may be achieved.

Another aspect of the present invention is directed to the use of an anionic polymer that is used as a bridging agent to enhance bonding between the cationic polysaccharide and the cationic therapeutic agents. In this aspect of the invention, the anionic polymers include, but are not limited to, glycosaminoglycans, such as, for example, including hyaluronan, hyaluronic acid and it's derivatives, heparin, chondroitin and keratin sulfates. Other anionic polymers include, for example, carboxymethyl cellulose, carboxymethyl starch, carboxymethyl guar and the like, as well as polyacrylic acid and it's derivatives. Such anionic polymer are commercially available.

The ratio of cationic polymer to anionic polymer can vary. In a preferred embodiment, after the anionic polymer is added to the cationic polymer, sufficient cationic charge remains on the polymer backbone to bind the polymer to the mucosal surface. The relative weight ratio of cationic polymer to anionic polymer can fall in the range of 0.01 to about 200:1, preferably from about 2:1 to about 100:1. The amount of cationic therapeutic agents can also vary in the aqueous-composition.

The cationic polymer and cationic therapeutic agents (and anionic polymers when employed) of this invention are typically provided to the mucosal surface in an aqueous solution typically neutral buffered and isotonic, similar to artificial tear solutions. The tonicity or osmolality can be either adjusted to hypotonicity, isotonicity or hypertonicity relative to the normal tear. Such tonicity agents are known in the art but not limited to nonionic agents include dextrose, mannitol glycerin and propylene glycol in amounts varying from 0.0% to 10.0% by weight in the final formulation. Preferably, the range in the level of isotonic salts employed is up to about 0.9 parts by weight for inorganic salts and up to about 6.0 parts by weight for organic substances. Illustrative inorganic isotonicizers include sodium chloride, boric acid and borax, while natural substance isotonicizers are generally sugars such as mannitol and sorbital. The pH of these isotonicized solutions is typically from about 3 to 9. When the delivery systems are for use in the eye, the pH of the composition should be as close as possible to neutral and within the range of pH 6–8.

Preservatives are commonly employed in most multi dosage ophthalmic formulations to prevent microbial contamination during use. Suitable preservatives include benzalkonium chloride, POLYQUAD® POLYQUJATERNTUM-1 available from Alcon Labs. Fort Worth, Tex., thimerosal, edetate disodium, chlorobutanol and the like. Typically, such preservatives are used in levels ranging from 0.001% to 1.0% by weight in the final composition. Thickeners are often added to ophthalmic preparations to produce desirable viscosities depending upon application. Common viscosifiers include hydroxyethyl cellulose, hydroxypropylmethyl cellulose, polyvinyl alcohol, polyvinyl pyrolidone, dextran, and the like. The selection and amount of other optional ingredients contained in the compositions of this invention are not critical but will vary depending upon the particular ingredient, composition and desired use level and may be any effective amount for achieving the desired property provided by such ingredients, following procedures known to those in the art.

Preferably, the cationic polysaccharides, cationic therapeutic agents and anionic polymers, when employed, are comprised in a pharmaceutically acceptable liquid carrier, preferably an aqueous liquid and more preferably water, which is clear, i.e., not cloudy so as to cause visual distortion or other visual problems. Quite surprisingly, it has been found in accordance with the present invention that the addition of a salt to the composition can enhance the clarity of composition. Indeed, in some cases, particularly when the anionic therapeutic agent is employed, clear solutions may not be obtained unless a salt is added to the composition.

The aqueous compositions of the present invention can be provided topically to the mucosal surface in any desired form, e.g., as a gel, lotion or cream. In a preferred aspect of the invention wherein the compositions are used to treat eye infirmities, drops are used to deliver the composition.

The compositions of the present invention are useful in any application where it is desired to deliver a cationic therapeutic agent to a mucosal surface, for example, in the treatment of lowering intraocular pressure and glaucoma or for the delivery of a drug to the nose, mouth, vagina or gastrointestinal tract.

The following specific examples illustrate certain aspects of the present invention and are set forth for illustration only and are not to be construed as limitations on the appended claims. All parts and percentages are by weight unless otherwise specified.

EXAMPLES

The following examples are representative of delivery systems in accordance with the present invention useful in the sustained release of cationic therapeutic agents for lowering and controlling IOP and glaucoma. These formulations also provide for amelioration of harsh therapeutic agents.

DEFINITIONS

The following designations used in the Examples and elsewhere herein have the following meaning:

Cationic Cellulosic (1)

Cationic cellulosic polymer (N,N,N-trimethyl ammonium chloride hydroxyethyl cellulose) with a molecular weight of less than about 500,000 g/mol and with greater than about 0.2 moles per mole of quaternary substitution available from Union Carbide Corporation, Danbury, Conn.

Cationic Cellulosic (2)

Cationic cellulosic polymer (N,N,N-trimethyl ammonium chloride hydroxyethyl cellulose) with a molecular weight of from about 500,000 to 800,000 g/mol and with greater than about 0.2 moles per mole of quaternary substitution available from Union Carbide Corporation, Danbury, Conn.

Cationic Cellulosic (3)

Cationic cellulosic polymer (N,N,N-trimethyl ammonium chloride hydroxyethyl cellulose) with a molecular weight of form about 500,000 to 800,000 g/mol and with about 0.2 or less moles per mole of quaternary substitution available from Union Carbide Corporation, Danbury, Conn.

Cationic Cellulosic (4)

Cationic cellulosic polymer (N,N,N-trimethyl ammonium chloride hydroxyethyl cellulose) with a molecular weight of greater than about 800,000 g/mol and with greater than about 0.2 moles per mole of quaternary substitution available from Union Carbide Corporation, Danbury, Conn.

Cationic Cellulosic (5)

Cationic cellulosic polymer (N,N,N-trimethyl ammonium chloride hydroxyethyl cellulose) with a molecular weight of greater than about 800,000 g/mol and with about 0.2 or less moles per mole of quaternary substitution available from Union Carbide Corporation, Danbury, Conn.

Na Hyaluronic Acid (HA)

Glycosaminoglycan with a molecular weight of approximately 2,000,000 available from Genzyme Corporation, Cambridge, Mass.

EXAMPLE 1

A formulation was prepared having the following composition.

| Ingredient | Concentration (wt/v %) | Amount (in 100 g solution) |
|---|---|---|
| Cationic Cellulosic (2) | 0.50 | 0.50 |
| Na Hyaluronic Acid | 0.05 | 0.05 |
| Pilocarpine HCl | 0.25 | 0.25 |
| Balanced salt solution | 100% | 100 |
| pH | 5.4 | |
| Kinematic viscosity (dl/g) | 26.5 | |

Procedure

A 0.5% solution of cationic cellulosic (2) and Na Hyaluronic Acid were prepared in a balanced salt solution at a weight ratio of 10:1. The pH of the solution was 7.2. To this clear and colorless solution, pilocarpine HCl (Sigma Chemical Co., St. Louis, Mo.) and the contents were allowed to mix for 1 hour. The contents remained clear and colorless with a pH=5.4. The solution was filter sterilized through a 0.22 $\mu$ cartridge (Millipore Corp., Bedford Mass.) at 25 ° C. The final solution viscosity was 26.5 dl/g.

ESCA Preparation:

A freshly cleaved piece of mica, an anionic, non-biological substrate was dipped for 30 seconds in the test solution, then immediately transferred into a first wash vial for 30 seconds, then repeated for a subsequent wash at 30 seconds. The sample was covered and allowed to air dry for 1 hour. The remaining water was removed by placing the sample in a prep chamber for 30 minutes under a vacuum of $10^{-6}$ torr. The mica sample was then mounted on a copper block which were placed on the ESCA stage using double-sided tape to ensure that the sample was fully floating. The same mica deposition and washing was performed on solutions containing pilocarpine alone as well as cationic cellulosic (2): HA at a 10:1 ratio.

ESCA Analysis

Figure 2:
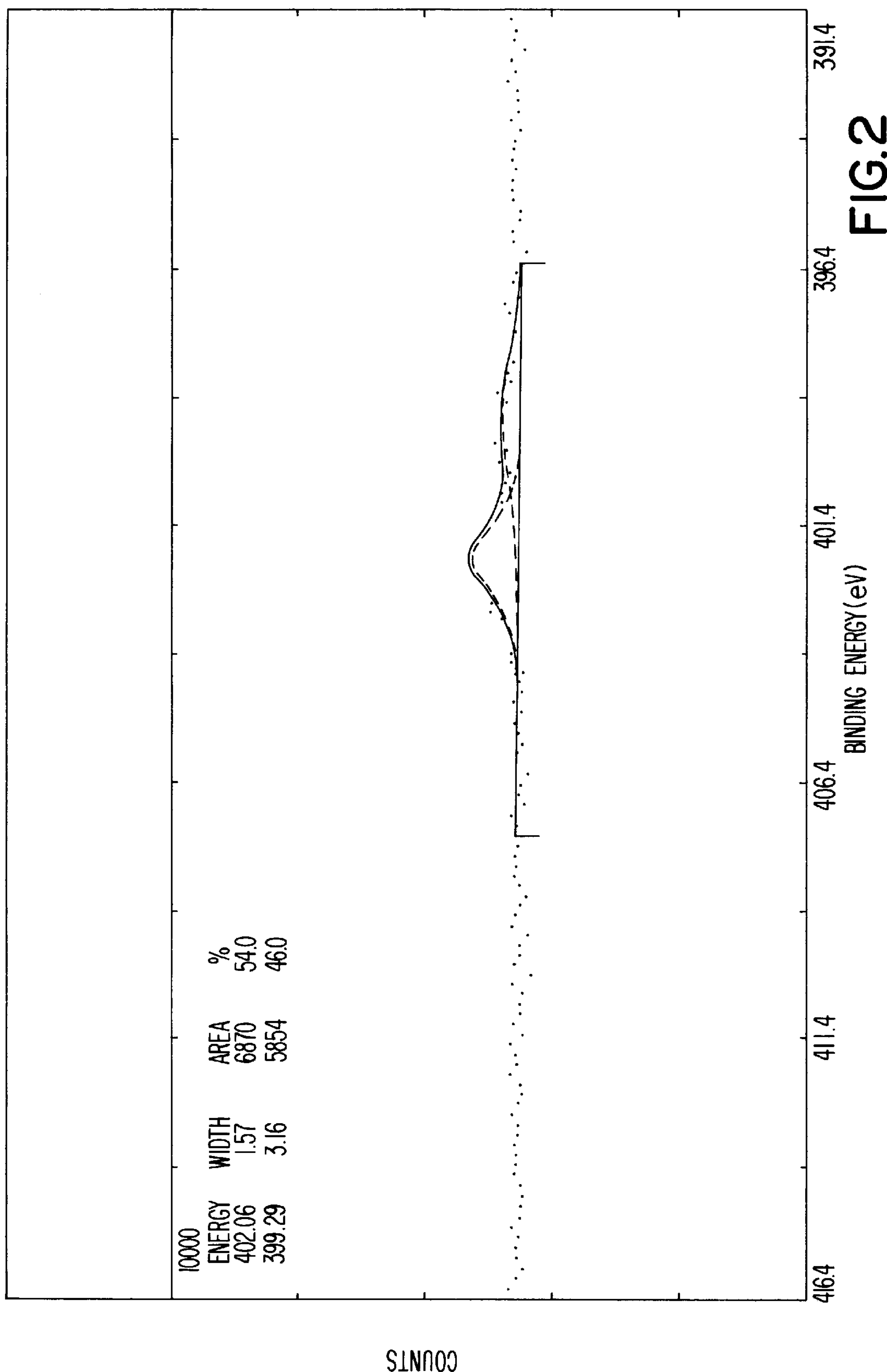
FIG. 2 is an ESCA spectrum of a high resolution scan from a cationic cellulosic and hyaluronic acids.
Figure 3:
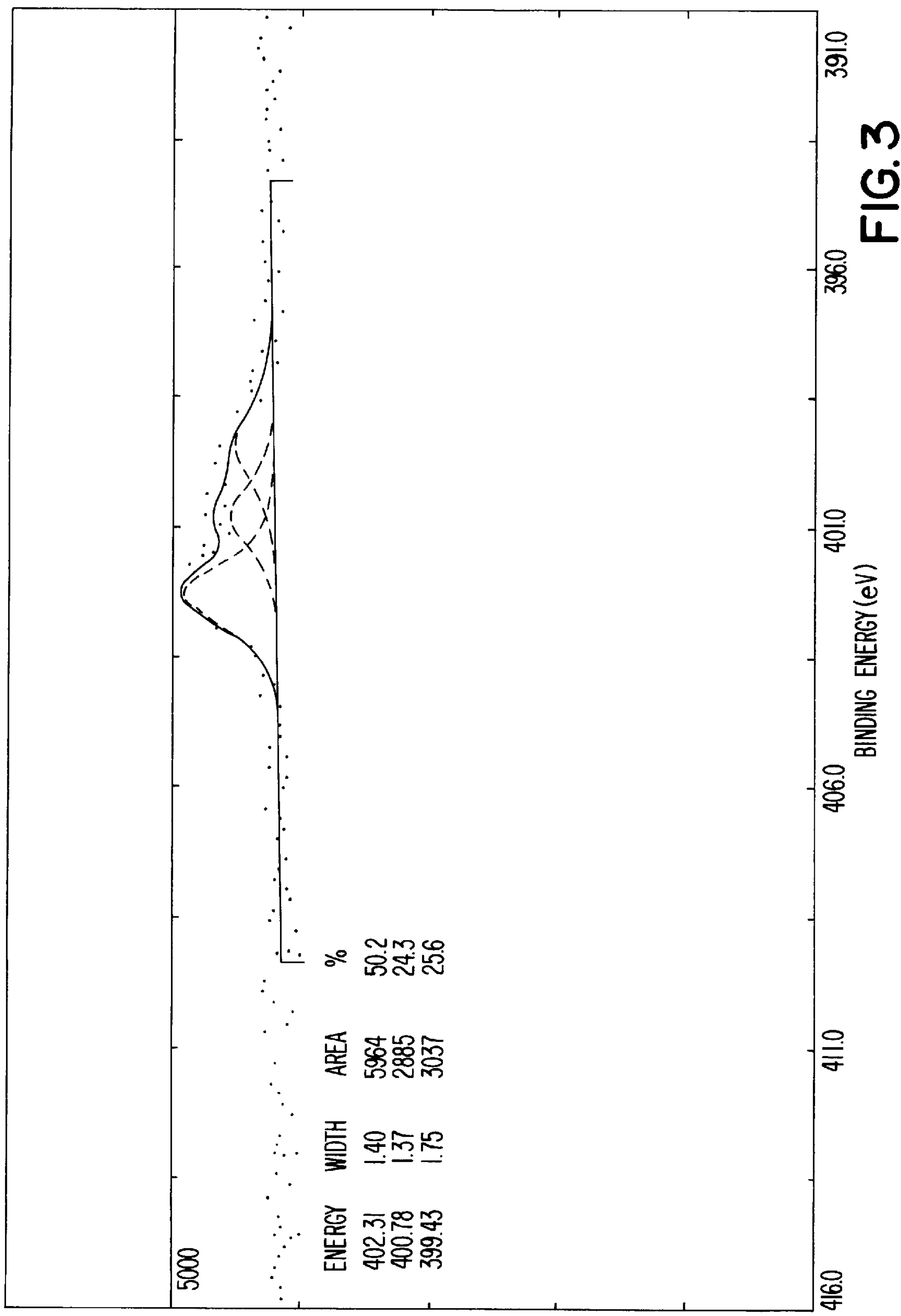
FIG. 3 is an ESCA spectrum of a high resolution scan from a cationic cellulosic, hyaluronic acid and pilocarpine HCl.

FIG. 1 is an ESCA spectrum of a high resolution scan from pilocarpine HCl revealing a distinct nitrogen signal at 400.78 eV. FIG. 2 is an ESCA spectrum of a high resolution scan from cationic cellulosic (2):HA pair at a 10:1 ratio. This spectrum reveals two distinct nitrogen signals at 402.51 eV and 399.78 eV indicative of the quaternary ammonium moiety of the cationic cellulosic and the N-acetyl group of the sodium hyaluronate. FIG. 3 is an ESCA spectrum of a high resolution scan from a cationic cellulosic (1):HA:pilocarpine HCl at a 10:1:1 ratio. This spectrum reveals three distinct nitrogen signals at 402.31 eV, 400.78 eV and 399.43 eV indicative of the quaternary ammonium moiety of the cationic cellulosic, the N-methyl imidazole ring of pilocarpine and the N-acetyl group of the sodium hyaluronate. This spectrum confirms that even after washing, the pilocarpine is still present on the mica surface via the anionic bridging agent which is electrostatically bound to the cationic cellulosic.

EXAMPLE 2

A formulation was prepared having the following composition.

| Ingredient | Concentration (wt/v %) | Amount in 100 g solution |
|---|---|---|
| Cationic Cellulosic (2) | 0.50 | 0.50 |
| Na Hyaluronic Acid | 0.05 | 0.05 |
| Mannitol | 3.3 | 3.3 |
| Carbachol | 0.25 | 0.25 |
| Benzalkonium chloride | 0.005 | 0.005 |
| Balanced salt solution | 100% | 100 |
| pH | 7.4 | |
| Kinematic viscosity (dl/g) | 27.7 | |

Procedure

A 0.5% solution of cationic cellulosic (2) and Na Hyaluronic Acid were prepared in a balanced salt solution at a weight ratio of 10:1. The pH of the solution was 7.4. To this clear and colorless solution, mannitol (Fisher Biotech., Fairlawn, N.J.) was added followed by carbachol (Sigma Chemical Co., St. Louis, Mo.). Benzalkonium chloride (Aldrich Chemical, Milwaukee, Wis.) was added as a preservative and the contents were allowed to mix for 1 hour. The contents remained clear and colorless with a pH=7.4. The solution was filter sterilized through a 0.22 $\mu$ cartridge (Millipore Corp., Bedford, Mass.) at 25° C. The final solution viscosity was 27.7 dl/g.

EXAMPLE 3

A formulation was prepared having the following composition.

| Ingredient | Concentration (wt/v %) | Amount in 100 g solution |
|---|---|---|
| Cationic Cellulosic (2) | 0.50 | 0.50 |
| Na Hyaluronic Acid | 0.05 | 0.05 |
| Epinephrine | 1.0 | 1.0 |
| Balanced salt solution | 100% | 100 |
| pH | 7.4 | |
| Kinematic viscosity (dl/g) | 27.0 | |

Procedure

A 0.5% solution of cationic cellulosic (2) and Na Hyaluronic Acid were prepared in a balanced salt solution at a weight ratio of 10:1. The pH of the solution was 7.2. To this clear and colorless solution, epinephrine (Sigma Chemical Co., St. Louis, Mo.) was added and the contents were allowed to mix for 1 hour. The contents remained clear with a final pH=6.0. The final solution viscosity was 27.0 dl/g.

EXAMPLE 4

A formulation was prepared having the following composition.

| Ingredient | Concentration (wt/v %) | Amount in 100 g solution |
|---|---|---|
| Cationic Cellulosic (2) | 0.50 | 0.50 |
| Na Hyaluronic Acid | 0.25 | 0.25 |
| Carbachol | 0.90 | 9.0 ml of a 10% solution |
| Balanced salt solution | 100% | 100 |
| pH | 7.4 | |
| Kinematic viscosity (dl/g) | 98.9 | |

Procedure

A 0.5% solution of cationic cellulosic (2) and Na Hyaluronic Acid were prepared in a balanced salt solution at a weight ratio of 2:1. The pH of the solution was 7.2. To this clear and colorless solution, an carbachol solution (Sigma Chemical Co., St. Louis, Mo.) was added and the contents were allowed to mix for 1 hour. The contents remained clear and colorless with a pH=7.4. The final solution viscosity was 98.9 dl/g.

EXAMPLE 5

A formulation was prepared having the following composition.

| Ingredient | Concentration (wt/v %) | Amount in 100 g solution |
|---|---|---|
| Cationic Cellulosic (2) | 0.50 | 0.50 |
| Na Hyaluronic Acid | 0.05 | 0.25 |
| Carbachol | 0.20 | 2.0 ml of a 10% solution |
| Balanced salt solution | 100% | 100 |
| pH | 7.2 | |
| Kinematic viscosity (dl/g) | 30.3 | |

Procedure

A 0.5% solution of cationic cellulosic (2) and Na Hyaluronic Acid were prepared in a balanced salt solution at a weight ratio of 10:1. The pH of the solution was 7.2. To this clear and colorless solution, an carbachol solution (Sigma Chemical Co., St. Louis, Mo.) was added and the contents were allowed to mix for 1 hour. The contents remained clear and colorless with a pH=7.2. The final solution viscosity was 30.3 dl/g.

EXAMPLE 6

A formulation was prepared having the following composition.

| Ingredient | Concentration (wt/v %) | Amount in 100 g solution |
| --- | --- | --- |
| Cationic Cellulosic (2) | 0.50 | 0.50 |
| Na Hyaluronic Acid | 0.10 | 0.10 |
| pilocarpine | 0.50 | 5.0 mL of a 10% solution |
| balanced salt solution | 100% | 100 |
| pH | 6.0 | |
| Kinematic viscosity (dl/g) | 48.8 | |

Procedure

A 0.5% solution of cationic cellulosic (2) and Na Hyaluronic Acid were prepared in a balanced salt solution at a weight ratio of 5:1. The pH of the solution was 7.2. To this clear and colorless solution, pilocarpine HCl (Sigma Chemical Co., St. Louis, Mo.) was added and the contents were allowed to mix for 1 hour. The contents remained clear and colorless with a final pH=6.0. The final solution viscosity was 48.8 dl/g.

Although the invention has been described above with respect to specific aspects, those skilled in the art will recognize that other aspects are intended to be included within the scope of the claims which follow. For example, although the application is generally directed to the delivery of cationic therapeutic agents to mucosal surfaces, those skilled in the art will recognize that the compositions and methods of the present invention can also be used to deliver cationic therapeutic agents to any body surface in the presence of mositure.

We claim:

1. A method for delivery of a cationic therapeutic agent to a mucosal surface, which method comprises providing a composition to said mucosal surface, said composition comprising:

(a) a pharmaceutically acceptable liquid carrier, (b) an effective amount of a cationic polysaccharide polymer substituted with greater than about 0.1 moles per mole of polysaccharide of a quaternary nitrogen compound having hydrocarbon substituents with from 1 to about 4 carbon atoms per substituent to provide substantivity to the mucosal surface, said cationic polysaccharide polymer being exclusive of anionic polymers selected from the group consisting of carboxymethyl cellulose, carboxymethyl starch, carboxymethyl chitin, carboxymethyl chitosan and carboxymethyl guar;

(c) an effective amount of a cationic therapeutic agent to provide delivery of the cationic therapeutic agent to the mucosal surface, said cationic therapeutic agent comprising an organic compound which bears or is capable of bearing a positive charge; and (d) an effective amount of an anionic polymer to enhance bonding between the cationic polysaccharide and the cationic therapeutic agent.

2. The method of claim 1 wherein the mucosal surface is the eye.

3. The method of claim 1 wherein the cationic polysaccharide polymer is a cationic cellulosic.

4. The method of claim 1 wherein the cationic therapeutic agent is selected from the group consisting of betaxolol, timolol, labetalol, propranolol, bupranolol, befunolol, acebutolol, salbutamol, atenulol, isoxaprolol, esmalol, pindolol, hepunolol, carpranolol, metaprolol, azotinolol, carteolol, diacetolol, epinephrine, pilocarpine, proepinephrine, norepinephrine, pronorepinephrine, clonidine and clonidine derivatives, carbachol and mixtures thereof.

5. The method of claim 1 wherein the anionic polymer is selected from the group consisting of hyaluronan, hyaluronic acid, hyaluronan derivatives, carboxymethyl cellulose, carboxymethyl starch, carboxymethyl chitin, carboxymethyl chitosan, carboxymethyl guar and poly(arylic acid).

6. The method of claim 1 wherein the effective amount of the cationic polysaccharide is from about 0.0025 to 20.0 wt % based on the total weight of the composition.

7. The method of claim 1 wherein the effective amount of the anionic polymer is from about 0.0001 to 5.0 wt % based on the total weight of the composition.

8. The method of claim 1 wherein the effective amount of the cationic therapeutic agent is from about 0.01–10.0 wt % is from about based on the total weight of the composition.

9. The method of claim 1 wherein the substitution level of the quaternary nitrogen compound is from about 0.1 to 1.0 mole per mole of the polysaccharide.

10. The method of claim 1 wherein the composition further comprises salt, preservatives, and tonicity agents.

11. The method of claim 1 wherein the relative weight ratio of the cationic polysaccharide polymer to cationic therapeutic agent is from about 1:1 to about 200:1.

12. The method of claim 1 wherein the relative weight ratio of the anionic polymer to cationic therapeutic agent is from about 1:1 to about 200:1.

13. The method of claim 10 wherein the composition has a viscosity of less than 100 centipoise.

14. A sustained release topic composition comprising:

(a) a cationic therapeutic agent comprising an organic compound which bears or is capable of bearing a positive charge;

(b) an effective amount of a cationic polysaccharide polymer substituted with greater than about 0.1 moles per mole of polysaccharide of a quaternary nitrogen compound having hydrocarbon substituents with from 1 to about 4 carbon atoms per substituent to provide substantivity to the mucosal surface, said cationic polysaccharide polymer being exclusive of anionic polymers selected from the group consisting of carboxymethyl cellulose, carboxymethyl starch, carboxymethyl chitin, carboxymethyl chitosan and carboxymethyl guar;

(c) an effective amount of an anionic polymer to enhance bonding between the cationic polysaccharide and the cationic therapeutic agent and (d) a pharmaceutically acceptable liquid carrier.

15. The composition of claim 14 wherein the anionic polymer is selected from the group consisting of hyaluronan, hyaluronic acid, hyaluronan derivatives, carboxy methyl cellulose, carboxymethyl starch, carboxymethyl chitin carboxymethyl chitosan, carboxymethyl guar, poly (acrylic acid) and mixtures thereof.

16. The composition of claim 15 wherein the concentration of the anionic polymer is from about 0.001 to 0.6 wt % based on the total weight of the composition.

17. The composition of claim 14 wherein the concentration of the cationic therapeutic agent is from about 0.001 to 0.5 wt % based on the total weight of the composition.

18. The composition of claim 14 wherein the cationic therapeutic agent has an affinity for one or both of the mucosal surface or the cationic polysaccharide.

19. A method of controlling intraocular pressure which comprises topically applying the composition of claim 14 to the eye.

20. A method of administering a cationic therapeutic agent to a body surface in the presence of moisture comprising providing with the cationic therapeutic agent a cationic polysaccharide having an affinity for the body surface and an effective amount of an anionic polymer to enhance bonding between the cationic polysaccharide and the cationic therapeutic agent, said cationic polysaccharide polymer being exclusive of anionic polymers selected from the group consisting of carboxymethyl cellulose, carboxymethyl starch, carboxymethyl chitin, carboxymethyl chitosan and carboxymethyl guar and said cationic therapeutic agent comprising an organic compound which bears or is capable of bearing a positive charge.

21. The method of claim 20 wherein said cationic therapeutic agent has an affinity for the cationic polysaccharide.

* * * * *